US00PP37731P2

(12) United States Plant Patent
Dirr et al.

(10) Patent No.: US PP37,731 P2
(45) Date of Patent: Oct. 6, 2026

(54) ***NANDINA* PLANT NAMED 'GS-02-21'**

(50) Latin Name: *Nandina domestica*
Varietal Denomination: GS-02-21

(71) Applicant: Premier Introductions Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 19/418,507

(22) Filed: Dec. 12, 2025

(51) Int. Cl.
*A01H 5/00* (2018.01)
*A01H 6/00* (2018.01)

(52) U.S. Cl.
USPC ..... Plt./235

(58) Field of Classification Search
USPC ..... Plt./235
See application file for complete search history.

(56) References Cited

U.S. PATENT DOCUMENTS

PP32,470 P2 * 11/2020 Zhang ..... A01H 6/00 Plt./235

* cited by examiner

*Primary Examiner* — Susan Mccormick Ewoldt
*Assistant Examiner* — Zachariah Allan Kay

(57) ABSTRACT

A new and distinct cultivar of *Nandina* plant named 'GS-02-21' is disclosed, characterized by its compact growing form and dense foliage, yellow new growth, yellow winter color that holds in the ground or in a container, and no notable diseases and pests. The new cultivar is a *Nandina*, typically produced as an outdoor ornamental plant.

3 Drawing Sheets

Latin name of the genus and species: *Nandina domestica*.
Cultivar denomination: 'GS-02-21'.

BACKGROUND OF THE INVENTION

The new *Nandina domestica* 'GS-02-21' is a product of a planned breeding program conducted by the inventors at a nursery in Watkinsville, Georgia. The objective of this *Nandina* breeding program is to create new plant cultivars with compact habits, and bright and colorful foliage in the spring and fall/winter.

'GS-02-21' originated in 2021 from open-pollinated seed of *Nandina domestica* 'Gulf Stream', U.S. Plant Pat. No. 5,656, as part of a breeding program in Watkinsville, Georgia. The cultivar 'GS-02-21' was selected in the year 2021 because of its short internodes, yellow foliage, yellow winter color that is persistent in the ground and in a container.

Vegetative reproduction of the new *Nandina domestica* 'GS-02-21' using terminal cuttings in controlled environment has been continued in Watkinsville, Georgia since 2021. Observations of the resulting 'GS-02-21' vegetatively propagated progeny have shown that the unique features of this new *Nandina domestica* 'GS-02-21' are stable and reproduced true to type in successive generations.

SUMMARY OF THE INVENTION

Plants of the new cultivar 'GS-02-21' have not been observed under all possible environmental conditions. The phenotype may vary somewhat with changes in light, temperature, soil and rainfall without, however, any variance in genotype.

The following traits have been repeatedly observed and are determined to be unique characteristics of 'GS-02-21'.

These characteristics in combination distinguish 'GS-02-21' as a new and distinct cultivar:

1. Compact growing form.
2. Dense foliage.
3. Yellow new growth.
4. Yellow fall and winter color that is persistent in a container or when planted in the ground.
5. No notable diseases and pests.

PARENT COMPARISON

Plants of 'GS-02-21' are similar to the seed parent plant *Nandina domestica* 'Gulf Stream' in most horticultural characteristics; however plants of 'GS-02-21' differ in the following:

1. Foliage of the new cultivar emerges yellow aging to green, whereas foliage of 'Gulf Stream' emerges with multi-colored hues of green, orange, copper, and reddish bronze.
2. Fall and winter foliage color of the new cultivar is yellow, while the fall and winter foliage color of 'Gulf Stream' is orange and red.
3. Plants of the new cultivar are more compact than plants of 'Gulf Stream'.

COMMERCIAL COMPARISONS

Plants of 'GS-02-21' can be compared to plants of the commercial cultivar *Nandina domestica* 'Lemon Lime', U.S. Plant Pat. No. 24,749. 'GS-02-21' is similar to 'Lemon Lime' in most horticultural characteristics; however plants of 'GS-02-21' differ in the following:

1. Plants of the new cultivar are smaller and more compact than plants of 'Lemon Lime'.

2. Foliage of the new cultivar has brighter and more consistent fall and winter color than foliage of 'Lemon Lime'.

Plants of 'GS-02-21' can be compared to *Nandina domestica* 'ZhNan102', U.S. Plant Pat. No. 32,470. 'GS-02-21' is similar to 'ZhNan102' in most horticultural characteristics; however plants of 'GS-02-21' differ in the following:

1. Foliage of the new cultivar holds its yellow color in the ground and in a container, while foliage of 'ZhNan102' does not maintain its color in the ground.

BRIEF DESCRIPTION OF THE PHOTOGRAPHS

The accompanying color photographs illustrate the foliage characteristics and the overall appearance of 'GS-02-21', showing the colors as true as it is reasonably possible to obtain in color reproductions of this type. Colors in the photographs may differ slightly from the color values cited in the detailed botanical description which accurately describe the colors of the new *Nandina*.

DETAILED BOTANICAL DESCRIPTION

Figure 1:
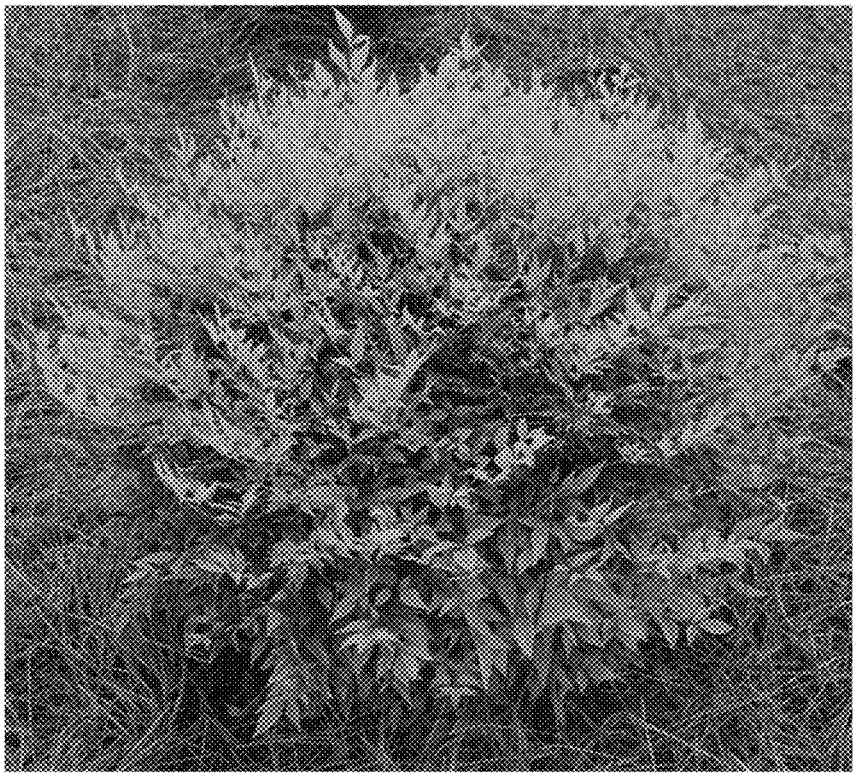
FIG. 1 illustrates the plant habit and fall foliage color, of a three-year-old 'GS-02-21' in the ground.
Figure 2:
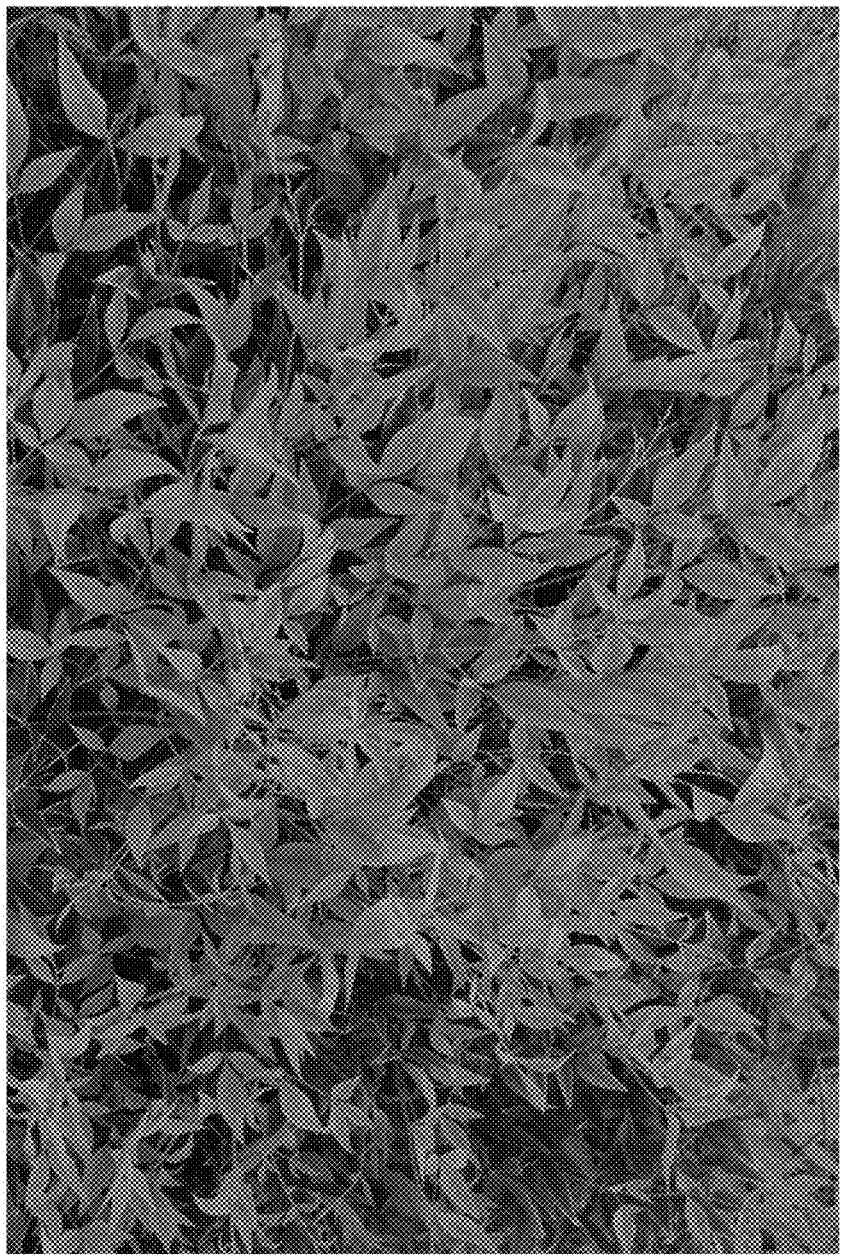
FIG. 2 illustrates the new growth of the foliage of a three-year-old plant of 'GS-02-21' in the ground.
Figure 3:
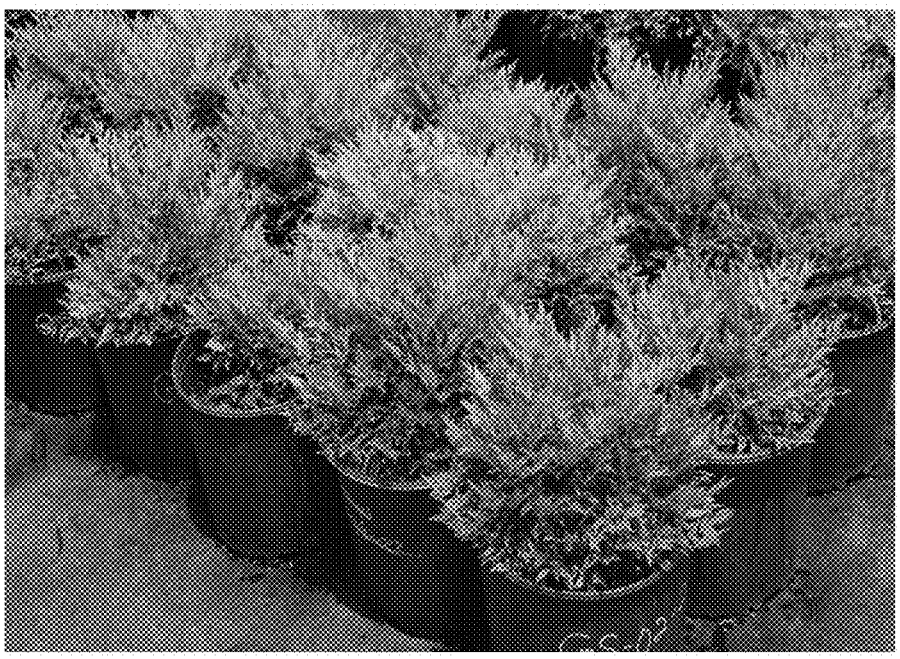
FIG. 3 illustrates container production of one-year-old plants of 'GS-02-21'.

In the following description, color references are made to The Royal Horticultural Society Colour Chart, 2015 Edition, except where general terms of ordinary dictionary significance are used. Plants used for the description were approximately two years old and were grown in 11.36 L containers under outdoor conditions in Watkinsville, Georgia.

Botanical classification: *Nandina domestica* 'GS-02-21'.

PROPAGATION

Typical method: Terminal cuttings and tissue culture.

Root initiation: Hardwood cuttings rooted in 3 to 5 weeks at 23° C. under mist.

Roots: White fibrous roots, dense, healthy, freely branching root system. Colored RHS White N155A.

PLANT

Plant type: Evergreen shrub.

Growth habit: Compact, mounding.

Shape: Dwarf with dense foliage.

Height: 30 cm from the soil level to the top of the foliage.

Plant spread: 45 cm.

Pot size of plant described: 11.36 L.

Age of plant described: Approximately 2 years.

Stem:

*Branching*.—Branches freely from basal buds.
*Number of lateral branches*.—20 to 30.
*Shape*.—Round.
*Color*.—Immature: RHS Yellow-Green N144A. Mature: RHS Green 137A.
*Length*.—12 cm.
*Width*.—2 mm.
*Aspect*.—Upright.
*Texture*.—Smooth.
*Pubescence*.—None.
*Internode length*.—2 to 3 cm.

FOLIAGE

Leaf:

*Arrangement*.—Alternate.
*Length*.—About 4 cm.
*Width*.—About 1 cm.
*Leaf type*.—Tri-pinnately compound.
*Leaflet number*.—Average 6 to about 12 per lateral branch.

Petiole:

*Length*.—2.5 cm.
*Diameter*.—1 mm.
*Color*.—Young: RHS Yellow-Green N144A. Mature: RHS Green 137A.

Petiolule:

*Length*.—1 mm.
*Diameter*.—1 mm.
*Color*.—Young: RHS Yellow-Green N144A. Mature: RHS Green 137A.

Leaflet:

*Base*.—Cuneate.
*Apex*.—Acute.
*Shape*.—Lanceolate.
*Margin*.—Entire.
*Venation pattern*.—Pinnate.
*Length*.—3 cm.
*Width*.—1 cm.
*Aspect*.—Cupped or reflexed.
*Color*.—Young, upper side: RHS Yellow-Green N144A. Young, under side: RHS Yellow-Green N144B. Mature, upper side: RHS Green 137A. Mature, under side: RHS Green 138A. Winter: Predominately RHS Yellow 7A with a hint of Yellow-Green 144A on upper surface and 151A on lower surface. The intense yellow foliage initiates in October and persists until about May in Watkinsville, Georgia.

FLOWER

Not observed to date.

REPRODUCTIVE ORGANS

Not observed to date.

OTHER CHARACTERISTICS

Fruit and seed: Not observed to date.

Disease resistance: Plants of the new *Nandina* have been observed to be resistant to diseases and pests common to *Nandina*.

Temperature and drought tolerance: Plants of the new *Nandina* have been observed to tolerate temperatures from about −11° C. to about 40° C. and have been observed to be tolerant to drought and full sun conditions. USDA Plant Hardiness Zones 6 to 9.

What is claimed is:

1. A new and distinct cultivar of *Nandina* plant named 'GS-02-21' as herein illustrated and described.

* * * * *